United States Patent [19]
Stadler et al.

[11] Patent Number: 5,495,852
[45] Date of Patent: Mar. 5, 1996

[54] METHOD AND APPARATUS FOR ESTIMATING DIAMETER OF AN ARTERY USING B-MODE ULTRASONIC IMAGES

[75] Inventors: Robert W. Stadler; W. Clem Karl, both of Cambridge; Robert S. Lees, Brookline, all of Mass.

[73] Assignee: Boston Heart Foundation, Cambridge, Mass.

[21] Appl. No.: 379,852

[22] Filed: Jan. 27, 1995

[51] Int. Cl.[6] .................................................. A61B 8/00
[52] U.S. Cl. ............................. 128/660.07; 128/661.100
[58] Field of Search ................. 128/660.070, 661.090, 128/661.100, 661.040, 654, 659, 713; 364/413.02, 413.22, 413.25

[56] References Cited

U.S. PATENT DOCUMENTS

| | | | |
|---|---|---|---|
| 4,790,322 | 12/1988 | Iinuma | 128/661.100 |
| 5,107,838 | 4/1992 | Yamaguchi | 128/713 X |
| 5,151,856 | 9/1992 | Halmann et al. | 364/413.03 |

*Primary Examiner*—Francis Jaworski
*Attorney, Agent, or Firm*—Cesari and McKenna

[57] ABSTRACT

An improved apparatus and method for measuring the diameter of an artery utilizes an ultrasonic imaging plane that is rotated slightly from the centerline of an artery to produce a "skew" image of the artery. The invention detects edge points on the image of near and far walls of the artery. It fits curves to the near and far end edge points and measures distances between the curves. Alternatively, it fits one curve to all the edge points and measures a parameter (such as minor diameter of an ellipse) of the curve. Finally, it estimates arterial diameter from the measurement.

11 Claims, 5 Drawing Sheets

METHOD AND APPARATUS FOR ESTIMATING DIAMETER OF AN ARTERY USING B-MODE ULTRASONIC IMAGES

FIELD OF THE INVENTION

The present invention relates to ultrasonic imaging systems and, in particular, to such systems for estimating diameter of an artery.

BACKGROUND OF THE INVENTION

Assessment of vascular physiology may be important in detecting and tracking atherosclerosis and it is also important in head failure, hypertension and diabetes research. Vascular physiology can be assessed, in part, through measurements of endothelial function and arterial compliance. Endothelial function can be assessed by measuring changes in the diameter of an artery in response to a stimulus such as change in blood flow velocity through the artery (more properly, a change in arterial wall shear stress). Endothelial function can be assessed by inflating a blood pressure cuff around a subject's forearm and monitoring velocity of blood flowing through a brachial artery while measuring the artery's diameter before, during and after the inflation of the cuff. Arterial compliance is a measure of change in diameter of an artery in response to a change in blood pressure within the artery.

Ultrasonic images commonly provide a basis for assessing vascular physiology. An ultrasonic imager utilizes a transducer to project an ultrasonic beam into a subject and receive echoes reflected from various anatomic features located within the subject. By timing the echoes, the imager calculates depths of the features and renders an image of the features on a display screen. An operator can then ascertain arterial diameter by measuring distances on the screen, such as a distance between "near" and "far" walls of an artery.

Ultrasonic imaging utilizes a finite "imaging plane" to display an image of a cross-section of a subject's anatomy. An ultrasonic imager constructs the image from echoes from features that the imaging plane intersects. An operator orients a transducer and, thereby, orients its associated imaging plane. The orientation of the imaging plane relative to an artery determines how the artery is represented in an image. For example, if a cross-sectional representation of an artery is desired, the operator orients the imaging plane perpendicular to the artery (herein referred to as "transverse imaging").

Two factors determine accuracy of arterial diameter estimates from "B-mode" images: how an image of an artery is acquired and how the diameter is calculated from the image. In "B-mode" ultrasonic images, brightness of a displayed feature is proportional to strength of echoes from the feature. Image acquisition depends on the skill of an operator and which representation (transverse, longitudinal, etc. ) of the artery is desired. In the prior art, an operator attempts to orient an imaging plane parallel to, and passing through the centerline of, an artery. This orientation (herein referred to as "longitudinal") represents the near and far walls as two parallel lines. The operator estimates diameter of the artery by measuring the distance between the two parallel lines. Specifically, the operator selects a point on each line and the imager calculates distance between the two points. The two points are commonly known as an "ultrasonic caliper." Problematically, diameter estimates made with ultrasonic calipers are suboptimal because they use only a fraction of available arterial wall edge information, and edge detection by the operator is subjective.

Longitudinal imaging of an artery generally provides more arterial wall information than transverse imaging because more of the imaging plane intersects relatively perpendicular features of the artery. The near and far walls are represented by lines in a longitudinal image but only by a small number of points in a transverse image. The lines in a longitudinal image thus provide more points on a display from which an operator can estimate diameter.

Problematically, diameter estimates of an artery made from longitudinal imaging planes tend to be underestimates due to deviation of the imaging plane from the centerline of the artery. In the prior art, an operator attempts to avoid underestimation by repeatedly reorienting the transducer, thereby reorienting the imaging plane, while searching for a combination of: 1) a largest representation of the artery, 2) a strongest set of echoes from near and far walls, thereby signifying perpendicular beam incidents, and 3) a best "7-zone" representation. An artery wall comprises several layers or "zones," which can appear in ultrasonic images of the artery. The "7-zone" appearance can only be obtained (in theory) when a longitudinal imaging plane passes through the centerline of an artery. Locating an imaging plane with a best 7-zone representation is difficult and requires subtle operator skill. Accordingly, an operator cannot assess accuracy of an estimate because he cannot prove that he acquired an image through the centerline of an artery.

Despite employing this three-pad strategy to avoid underestimation, errors in diameter estimates are likely because longitudinal imaging is sensitive to lateral movement of an artery relative to the transducer. Arteries commonly displace relatively large distances in response to stimuli (e.g. application of a blood pressure cuff) used during endothelial reactivity measurements. Lateral movement of an artery a distance of only 10% of an arterial diameter (0.4 mm for a medium-sized 4 mm vessel) relative to the imaging plane results in a 2% error in the diameter measurement.

It is, therefore, an objective of the present invention to provide increased accuracy in ultrasonic diameter estimates of an artery. It is a further objective to provide accurate arterial diameter measurements from images that are temporally spaced, i.e. to provide estimates that are insensitive to lateral movements of a transducer, subject or artery between the first and subsequent images. It is a yet further objective to enable an operator to ascertain whether an arterial diameter estimate is inaccurate due to mispositioning of an imaging plane relative to an artery.

SUMMARY OF THE INVENTION

The present invention, an improved arterial diameter measurement apparatus and method, utilizes an ultrasonic imaging plane that is rotated slightly (approximately 10°) from the centerline of an artery to produce an image of the artery. (This orientation of the imaging plane relative to the artery is herein referred to as "skew.") Theoretically, a skew image represents a cylindrical artery as an ellipse. Hence, a skew image represents an artery as having curved near and far walls. Utilizing edge detection techniques, the invention locates a set of edge points on each wall. It then fits a curve to each set of edge points (thus providing two curves) and it measures the distance between the two curves. Finally, it estimates diameter of the artery from the measured distance between the curves.

Alternately, the invention fits one curve to all the edge points and estimates diameter of the artery from a parameter of the curve. For example, when the curve is an ellipse, the diameter estimate is obtained from a minor axis of the ellipse.

Skew images advantageously provide nearly as much arterial wall information as longitudinal images. Relatively large portions of near and far walls are relatively perpendicular to an incident ultrasonic beam and produce strong echoes. As skew angle increases, a skew image provides progressively less arterial wall information. The information decreases to only a few points when the skew angle is 90° (i.e., in a transverse image).

However, skew images avoid the underestimation problem associated with longitudinal images because, barring a gross error in positioning the transducer, a skew imaging plane always passes through the centerline of an artery. In contrast to a longitudinal imaging plane, a skew imaging plane is guaranteed to intersect the centerline of an artery because it "cuts across" the artery. FIG. 1 illustrates a skew imaging plane 100 intersecting an artery 102 having a near wall 104 and a far wall 106. The resulting skew image represents near wall 104 as a curved line 108 and it represents far wall 106 as a curved line 110. The walls and lines have finite thickness. Boundaries between adjacent layers of a wall and the boundary between the wall and blood within the artery can each produce echoes. Curved lines 108 and 110 have regions 112 and 114, respectively, where the curvature is minimal. Regions 112 and 114 represent a diameter of artery 102 and correspond to the intersection of imaging plane 100 and the centerline of artery 102.

Skew images are generally insensitive to lateral movement of an artery relative to a transducer. Diameter estimates are therefore accurate as long as the centerline of the artery intersects the imaging plane. The centerline will generally continue to intersect the imaging plane despite lateral movements during a series of images because the imaging plane is large relative to expected translation of the artery. In any case, an operator can ascertain when the imaging plane no longer intersects the centerline and can then make appropriate adjustments.

The invention models an artery according to an expected representation of an image of the artery. When an imaging plane intersects an anatomic feature whose cross-sectional shape is known, geometry predicts a shape for a resulting image. Knowledge of the feature's composition and practical experience with ultrasonic imaging refines the predicted shape into an expected shape. Fitting an expected shape to scattered data points from an image facilitates incorporating all available edge information into a single measurement, e.g. diameter. This principle also applies to other echo-ranging systems, e.g. sonar and radar, and to non-anatomic features, e.g. buried pipelines and geologic and oceanographic features.

BRIEF DESCRIPTION OF THE DRAWINGS

The above and further advantages of the invention may be better understood by referring to the following description in conjunction with the accompanying drawings and which.

DESCRIPTION OF THE PREFERRED EMBODIMENT

Figure 1:
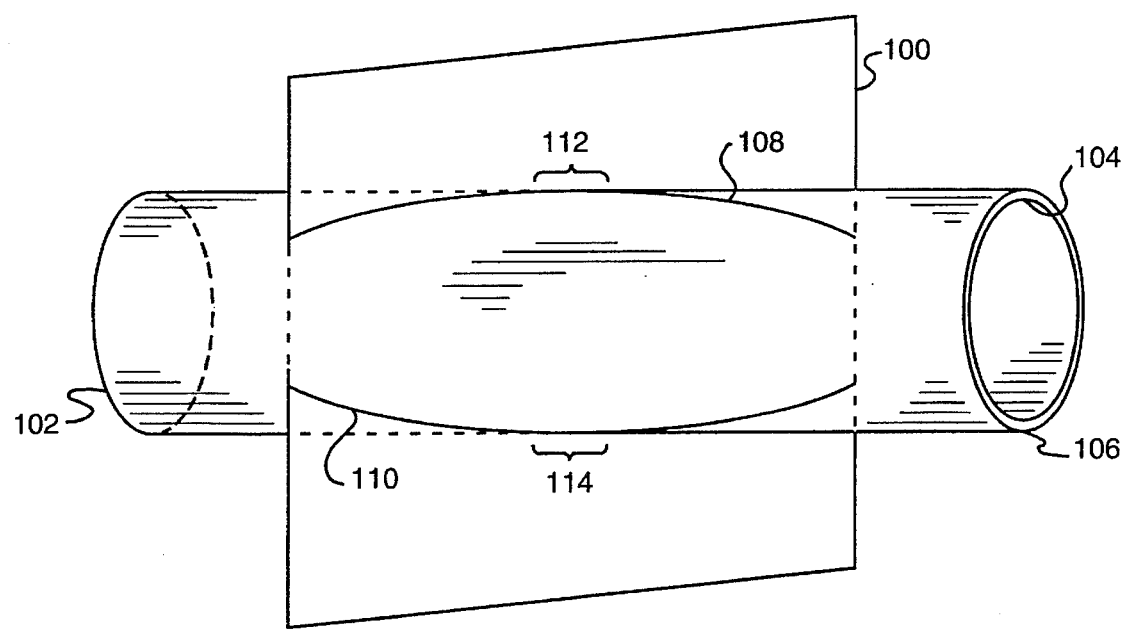
FIG. 1 illustrates a skew imaging plane intersecting an artery.
Figure 2:
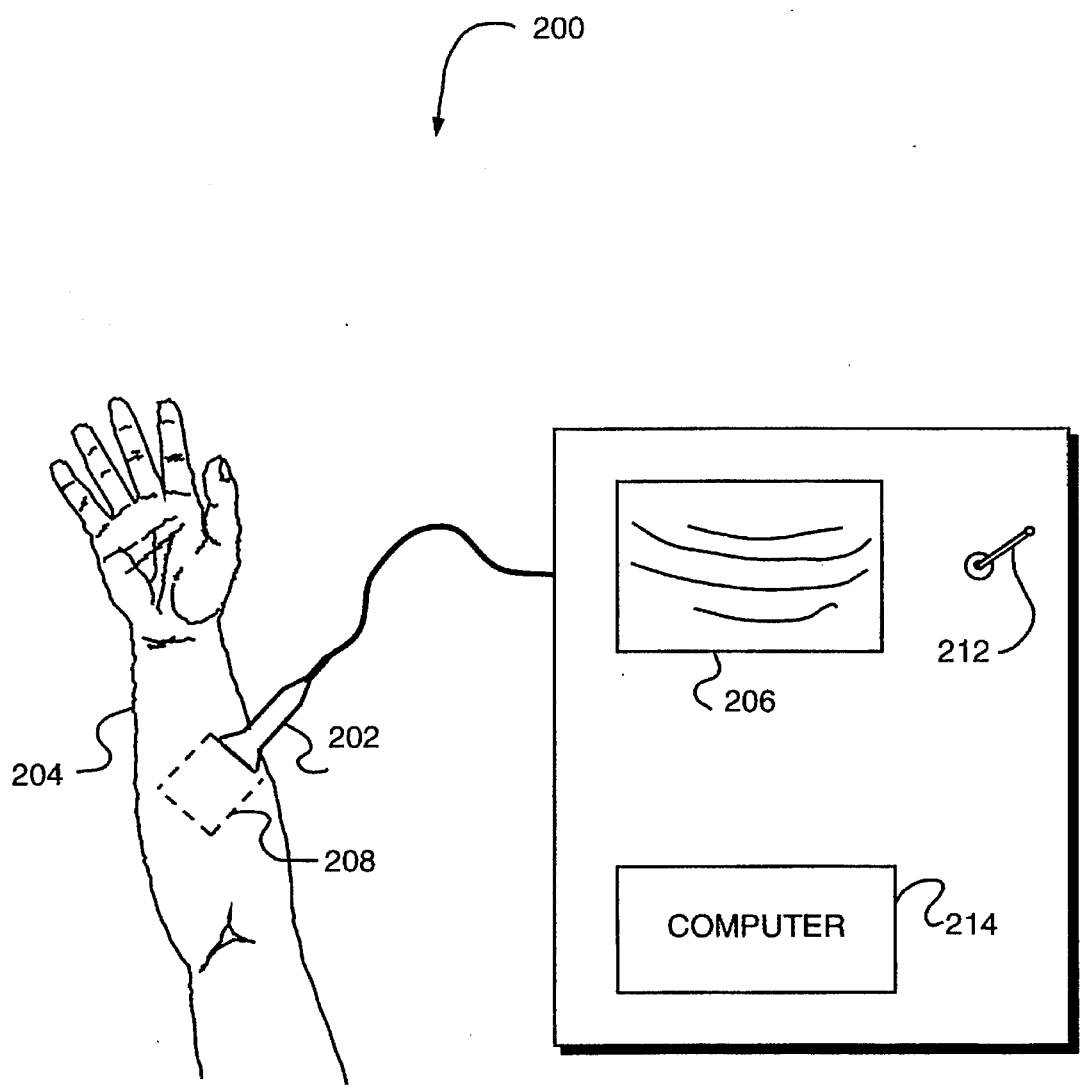
FIG. 2 is a diagram of an ultrasonic imager that incorporates the invention.

FIG. 2 is a diagram of an ultrasonic imager 200 that incorporates the invention. The imager 200 has a transducer 202 for acquiring an image from a subject 204 and a display screen 206 for displaying the image. Transducer 202 provides an imaging plane 208. Using a pointing device, such as a joystick 212, an operator can select points on the image. Software that performs edge detection, curve fitting and diameter estimation runs on a computer 214. Computer 214 receives signals from transducer 202 and joystick 212 and it provides an arterial display on the screen 206.

In the preferred embodiment, the invention models near and far walls of an artery in a skew image as two similar parabolas. That the curvatures are the same is somewhat counterintuitive. Geometry predicts that the two parabolas have opposite curvature, i.e. the two parabolas "face" each other. Experiments on brachial arteries, however, show that the preferred model generally produces more accurate estimates of arterial diameter than models employing oppositely-curved parabolas or an ellipse, probably because the arteries are not straight but have bends in regions of measurement. Other arteries may be better suited by different models, e.g. ellipses or hyperbolas. An operator is generally an excellent judge of the model that best fits a given image.

The operator uses transducer 202 to acquire an image of an artery. The operator observes the image on display screen 206 and initially utilizes the three-part strategy described earlier to acquire a best longitudinal image of an artery. He then repositions transducer 202 so as to rotate imaging plane 208, preferably about 10°, from the centerline of the artery while ensuring that imaging plane 208, intersects the centerline of the artery and thus providing the desired skew image of the artery. The operator then selects preliminary edge points on the image of the artery and then computer 214 uses a well-known edge detection algorithm to refine the edge points.

Figure 3:
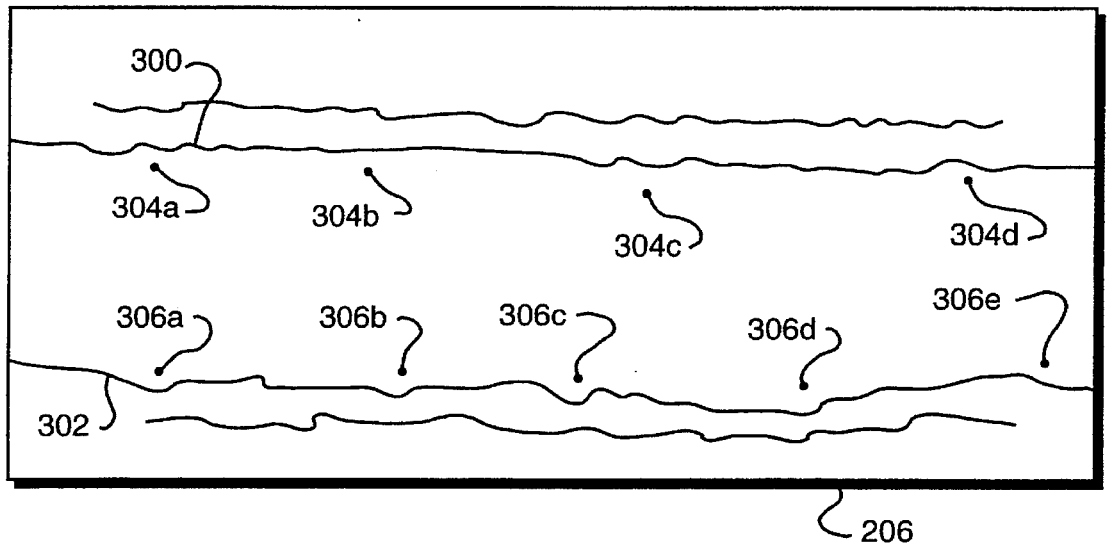
FIG. 3 illustrates an image of an artery displayed on the ultrasonic imager of FIG. 2.
Figure 4:
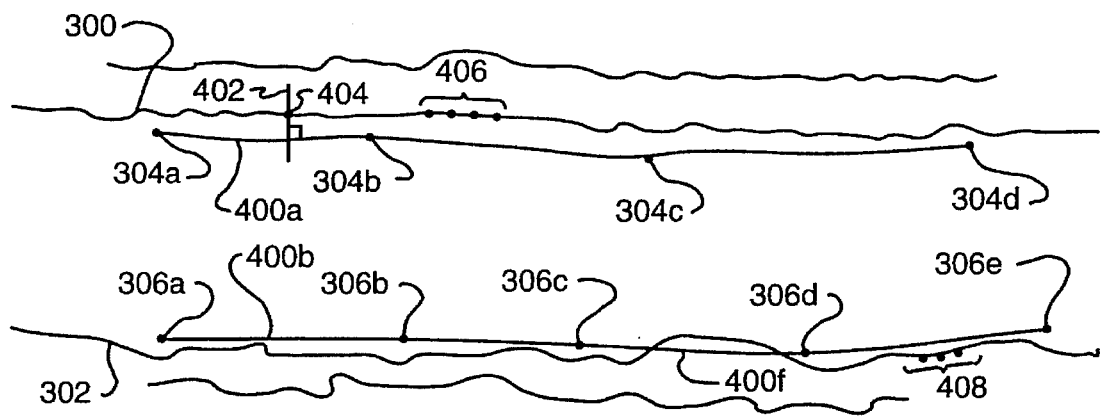
FIG. 4 illustrates splines and refined edge points on an image of an artery.

More specifically, FIG. 3 illustrates a skew image of an artery displayed on display screen 206. The image has a near wall edge 300 and a far wall edge 302. For measurement of the inner diameter of the artery, the operator uses joystick 212 to select several preliminary edge points 304a–d proximate to the near wall edge 300 and preliminary edge points 306a–e proximate to the far wall edge 302. As shown in FIG. 4, computer 214 fits splines 400a and 400b (each typically consisting of 100 points) to the sets of preliminary edge points 304a–d and 306a–e. A spline is a smooth curve that connects selected points. For each point in splines 400a and 400b, computer 214 then calculates a direction perpendicular to the spline, e.g. perpendicular 402. Using well-known techniques, computer 214 then interpolates intensity values of image pixels along the perpendicular, filters the interpolated values, and chooses a refined edge point 404. Specifically, computer 214 chooses a point with a largest weighted sum of first and second derivatives of intensity as a refined edge point. By this method, computer 214 chooses upper and lower sets of refined edge points, such as those indicated fragmentarily at 406 and 408, for the near and far walls.

Computer 214 then fits curves to the refined edge points. Assume that computer 214 chose $N_n$ refined near edge points and $N_f$ refined far edge points and that these points have coordinates $(X_{ni}, Y_{ni})$, i=1, ..., $N_n$, and $(x_{fi}, y_{fi})$, i= 1, ..., $N_f$, respectively. These points should satisfy a system of equations for a pair of parabolas:

$$y_{ni}=a x^2_{ni} + b_n x_{ni} + c_n, \quad i=1, \ldots, N_n \qquad (1)$$

$$y_{fi}=a x^2_{fi} + b_f x_{fi} + c_f, \quad i=1 \ldots, N_f \qquad (2)$$

Using well-known techniques, computer 214 solves the system of equations for parameters a, b, and c in a weighted least-squares sense to fit the model to the refined edge points. That is, the weights are in accord with the sharpnesses of the detected edges.

Figure 5:
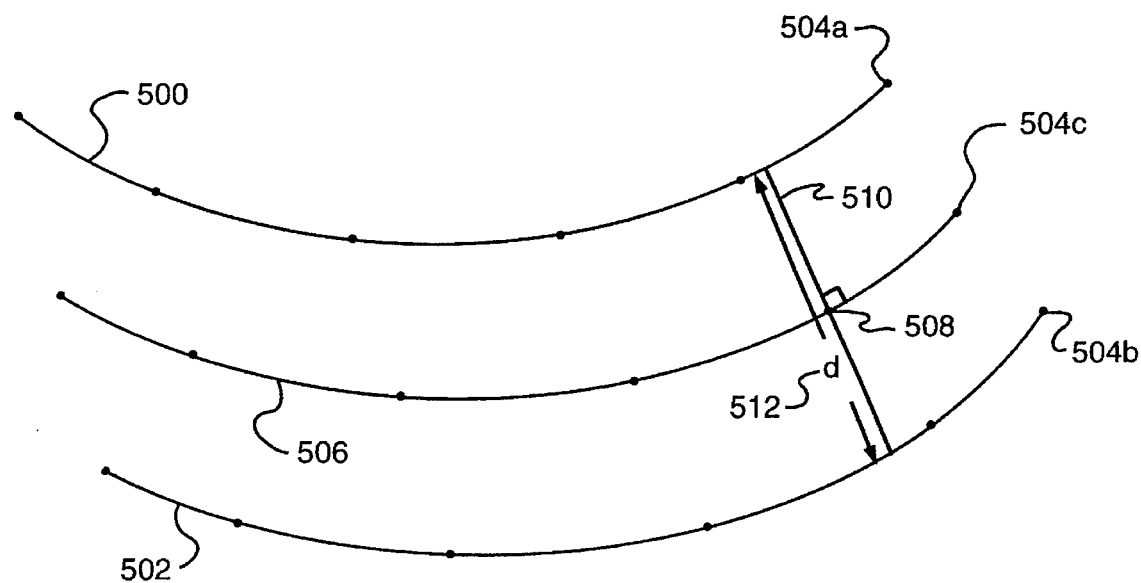
FIG. 5 illustrates distance measurements performed by the invention.

Finally, computer 214 averages the distances between the two curves at a number of locations to estimate the diameter of the artery. FIG. 5 depicts fitted curves 500 and 502. For pairs of corresponding points, such as points 504a and b, in curves 500 and 502 computer 214 averages their x co-ordinates and their y co-ordinates to calculate x and y co-ordinates for a center point, such as center point 504c. The center points collectively define a center line 506. For each center point, such as center point 508, computer 214 calculates the direction of a line, such as line 510, that is perpendicular to center line 506 and that intersects the center point. Computer 214 calculates a length, such as "d" 512, of the perpendicular line. Finally, computer 214 averages all the lengths to estimate the diameter of the artery.

The resulting diameter measurement is more accurate than measurements using prior techniques and perhaps more importantly, measurements made by means of the invention are more consistent. That is, repeated measurements of the same artery provide consistent results. Variations in the measured diameter of an artery therefore result more from changes in the artery and less from measurement artifacts than in prior systems.

It will be appreciated that the invention is useful for measurement of arterial diameters other than the inner diameter. That is, it can be used to measure diameters associated with various layers of the arterial wall. Furthermore, numerous changes can be made in the system specifically described herein without departing from the scope of the invention. For example, while the skew angle of the imaging plane is about 10°, the advantages of the invention can be obtained for a wide rage of skew angles, with the advantages diminishing as the angle approaches 0° (longitudinal imaging) and 90° (transverse imaging). We therefore prefer to operate within a skew angle range of 5° to 25°.

What is claimed is:

1. Apparatus for estimating diameter of an artery having a centerline and an inner wall, comprising:
    (a) means for acquiring an ultrasonic image of the artery, the image-acquiring means having an imaging plane, the image-acquiring means being positioned so as to orient the imaging plane skew to the artery, whereby it intersects the centerline of the artery;
    (b) edge-detecting means, coupled to the image-acquiring means, for detecting a plurality of near-edge points and a plurality of far-edge points on the acquired image of the artery;
    (c) curve-fitting means, coupled to the edge-detecting means, for fitting a first curve to the plurality of near-edge points and a second curve to the plurality of far-edge points; and
    (d) means, coupled to the curve-fitting means, for measuring at least one distance between the first and second curves and for estimating diameter of the artery from the at least one distance.

2. The apparatus, defined in claim 1, wherein the first and second curves are parabolas.

3. The apparatus, defined in claim 1, wherein the first curve is a portion of a hyperbola and the second curve is a portion of a hyperbola.

4. Apparatus for estimating diameter of an artery having a centerline and an inner wall, comprising:
    (a) means for acquiring an ultrasonic image of the artery, the image-acquiring means having an imaging plane, the image-acquiring means being positioned so as to orient the imaging plane skew to the artery, whereby it and intersects the centerline of the artery;
    (b) edge-detecting means, coupled to the image-acquiring means, for detecting a plurality of edge points on the acquired image of the artery;
    (c) curve-fitting means, coupled to the edge-detecting means, for fitting a curve to the plurality of edge points; and
    (d) measuring-and-estimating means, coupled to the curve-fitting means, for measuring at least one parameter of the curve and for estimating diameter of the artery from the at least one parameter.

5. The apparatus defined in claim 4, wherein:
    (a) the curve is an ellipse having a minor axis;
    (b) the parameter is length of the minor axis, and
    (c) the measuring-and-estimating means estimates diameter of the artery by multiplying the length of the minor axis by two.

6. A method of estimating diameter of an artery having a centerline and an inner wall, comprising the steps:
    (a) employing an ultrasonic imager that utilizes an imaging plane to acquire an image;
    (b) positioning the imaging plane skew to the artery, whereby it intersects the centerline of the artery;
    (c) acquiring an image of the artery;
    (d) detecting a plurality of near-edge points and a plurality of far-edge points on the image of the artery;
    (e) fitting a first curve to the near-edge points and a second curve to the far-edge points;
    (f) measuring at least one distance between the first and second curves; and
    (g) estimating diameter of the artery from the at least one distance measured in step (f).

7. The method defined in claim 6, wherein the first and second curves are parabolas.

8. The method defined in claim 6, wherein the first and second curves are hyperbolas.

9. A method of estimating diameter of an artery having a centerline and an inner wall, comprising the steps:
    (a) employing an ultrasonic imager that utilizes an imaging plane to acquire an image;
    (b) alternately acquiring an image of the artery and changing orientation of the imaging plane relative to the artery until the imaging plane is skew to the artery, whereby the imaging plane intersects the centerline of the artery;
    (c) detecting a plurality of near-edge points and a plurality of far-edge points on the image of the artery;
    (d) fitting a first curve to the near-edge points and a second curve to the far-edge points;
    (e) measuring at least one distance between the first and second curves; and
    (f) estimating diameter of the artery from the at least one distance measured in step (f).

10. The method defined in claim 9, wherein the first and second curves are parabolas.

11. The method defined in claim 9, wherein the first and second curves are hyperbolas.

* * * * *

UNITED STATES PATENT AND TRADEMARK OFFICE
CERTIFICATE OF CORRECTION

PATENT NO. : 5,495,852

DATED : March 5, 1996

INVENTOR(S) : Robert W. Stadler, et al.

It is certified that error appears in the above-identified patent and that said Letters Patent is hereby corrected as shown below:

Column 1, line 15, delete "head" and insert --heart--.

Column 2, line 29, delete "pad" and insert --part--.

Column 5, formula (1), that portion of the formula reading $ax^2_{ni}i$ should read $ax^2_{ni}$ Signed and Sealed this Third Day of September, 1996

BRUCE LEHMAN

Attesting Officer     Commissioner of Patents and Trademarks